United States Patent [19]

Nieh

[11] Patent Number: 4,569,798

[45] Date of Patent: Feb. 11, 1986

[54] AMPHOTERIC SURFACE ACTIVE MONOMERS

[75] Inventor: Edward C. Y. Nieh, Austin, Tex.

[73] Assignee: Texaco, Inc., White Plains, N.Y.

[21] Appl. No.: 449,960

[22] Filed: Dec. 15, 1982

[51] Int. Cl.$^4$ ............... C07C 69/40; C07C 101/34
[52] U.S. Cl. ............... 260/501.13; 560/170; 560/196; 260/404.5
[58] Field of Search ............... 560/170, 196; 260/404.5 PN, 501.13

[56] References Cited

U.S. PATENT DOCUMENTS 3,839,419 10/1974 Samour et al. .................. 560/196
4,228,042 10/1980 Letton .............................. 560/196

Primary Examiner—James H. Reamer
Attorney, Agent, or Firm—Robert A. Kulason; Jack H. Park; Richard A. Morgan

[57] ABSTRACT

Amphoteric surface active monomers and monomer solutions are revealed.

The monomers are synthesized by reacting a tertiary amine substituted acrylamide, an alkylene oxide and a succinic anhydride compound in aprotic polar solvent.

These compositions are useful for their surface activity and their ability to copolymerize with water soluble vinyl monomers and impart surface activity to the resulting copolymer. The monomers and copolymers thereof may be used as flocculants or for stabilizing polymeric latex.

10 Claims, No Drawings

AMPHOTERIC SURFACE ACTIVE MONOMERS

FIELD OF THE INVENTION

The invention relates to amphoteric vinyl monomers that have surfactant properties. These vinyl monomers are the condensation product of a tertiary amine substituted acrylamide, an alkylene oxide and a succinic anhydride compound.

PRIOR ART

Amphoteric compounds are those which contain both an anionic and a cationic hydrophilic group, and a hydrocarbon hydrophobic group. Typically the cationic portion is a quaternary ammonium derivative while the anionic portion can be a carboxylate, a sulfonate or a sulfate group.

Latex is produced by emulsion polymerization in aqueous solution. Latex product is typically kept in aqueous solution until final use, but these solutions are metastable and tend to coagulate or separate, an undesirable property. These metastable solutions suffer destabilization by such varying stimuli as contact with electrolyte or organic solvent, mechanical effects and thermal effects such as freezing.

In the past, emulsion phase stabilizers have been developed that are designed to neutralize thermodynamic unstability in such solutions. Such phase stabilizers are typically highly polar monomers which form synthetic lattices which dissipate disruptive stimuli and hence prevent the untoward effects associated therewith.

U.S. Pat. No. 3,959,355 discloses quaternary ammonium salts, used for latex stabilization, of the formula:

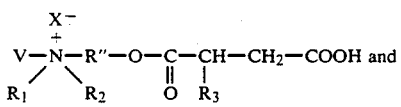

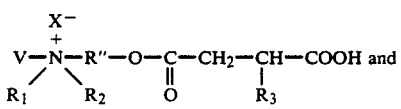

wherein V is:

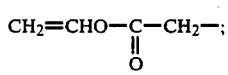

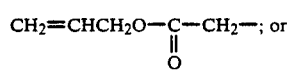

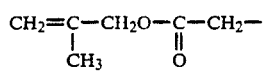

These compounds are distinguished from those of the present invention in two ways. First, the unsaturated group V is much less reactive in free radical polymerization than monomers of the present invention. That is, the unsaturated group V lacks resource activity in free radical polymerization compared with the alpha, beta unsaturated carbonyl group in monomers of the present invention. When V is an allyl or beta-methyl allyl ester, monomers of the prior art polymerize with difficulty and give products of low molecular weight. It is also known that the presence of such allyl monomers often tend to retard both the rate and degree of polymerization in reactions in which other comonomers are involved. (R. H. Yocum and E. B. Nyquist, *Functional Monomer*, Vol. 1, page 384 Marcel Dekker, Inc., N.Y 1973 and R. C. Laible, Chem. Rev. 58 807 (1958)).

Second, these compounds are salts, such as halide or sulfate salts, whereas compounds of the present invention are inner salts wherein the charge on the quaternary nitrogen is neutralized by the covalently bonded carboxy anion and not by a halide or sulfate anion.

U.S. Pat. No. 4,212,820 discloses cationic, surface active monomers. Harry Distler, *Mechanism of Reactions of Sulfur Compounds*, Vol. 4, 1969 pages 11–12 mentions a reaction of a tertiary amine substituted monomer, tetrahydrophthalic anhydride and ethylene oxide.

SUMMARY OF THE INVENTION

The present invention is a composition of matter which is the condensation product of:

(a) a tertiary amine substituted acrylamide of the general formula:

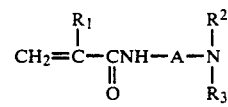

wherein
$R_1$ is hydrogen or methyl,
$R_2$ and $R_3$ are independently alkyls of from 1 to 3 carbon atoms and
A is a linear alkyl of from 2 to 3 carbon atoms;

(b) an alkylene oxide; and (c) a succinic anhydride compound.

These amphoteric monomers are useful as surfactants in reducing surface and interfacial tension in aqueous solutions over a wide pH range.

The monomers are particularly useful for the preparation of water soluble copolymers that have surface active properties.

DESCRIPTION OF THE PREFERRED EMBODIMENTS

In one aspect the present invention is a composition of matter of the formula:

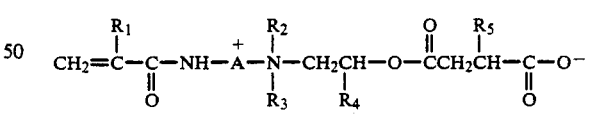

wherein
$R_1$ is selected from the group consisting of hydrogen and methyl,
$R_2$ is an alkyl of from 1 to 3 carbon atoms,
$R_3$ is an alkyl of from 1 to 3 carbon atoms,
$R_4$ is selected from the group consisting of hydrogen and methyl,
$R_5$ is an alkyl or alkenyl of from 9 to 21 carbon atoms, and,
A is a linear alkyl of from 2 to 3 carbon atoms.

Amphoteric surface active monomers of this configuration are conveniently produced by a simple synthesis. Typically a tertiary amine substituted acrylamide monomer is reacted with ethylene oxide or propylene oxide and an alkenyl succinic anhydride in aprotic polar solvent such as acetone, ethyl acetate, tetrahydroforan, dimethylformamide, acetonitrile, etc. at temperatures of about 40° C. to about 90° C. and pressures sufficient to keep all components in the liquid phase. The reaction proceeds to completion without catalyst. Optionally a trace of water or other protic solvent can be employed as an initiator. Reaction is typified by the sequence:

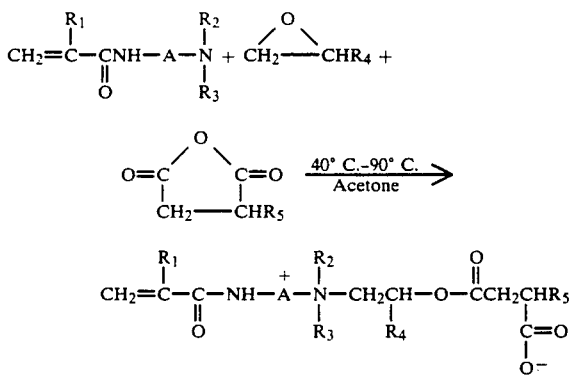

This new composition of matter is an inner salt wherein the charge on the quaternary nitrogen is neutralized by the covalently attached carboxy anion. It has been found that surfactants of this configuration are useful in reducing surface and interfacial tension in aqueous media over a wide pH range.

The present invention also relates to aqueous solutions comprising water and from about 0.01 wt % to 20 wt % or more of a monomer characterized by the general formula:

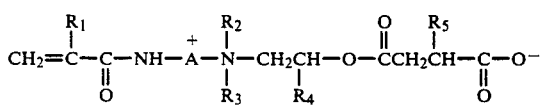

wherein
- $R_1$ is selected from the group consisting of hydrogen and methyl,
- $R_2$ is an alkyl of from 1 to 3 carbon atoms,
- $R_3$ is an alkyl of from 1 to 3 carbon atoms,
- $R_4$ is selected from the group consisting of hydrogen and methyl,
- $R_5$ is an alkyl or alkenyl of from 9 to 21 carbon atoms, and
- A is a linear alkyl of from 2 to 3 carbon atoms.

These aqueous solutions display surface and interfacial surface activity as demonstrated in Example 2. These solutions may comprise latex and optionally pigmentation for paint applications. Alternately these aqueous solutions may comprise brine for such applications such as secondary oil recovery or detergent adjuvants for cleaning purposes.

These amphoteric monomers exhibit surfactant properties in aqueous solution in concentrations ranging from 0.01 wt% and higher depending upon the mode of application. The minimal concentration of these products employed in commercial use is about 0.01 wt% to about 0.1 wt% while the upper concentration, which is limited almost entirely by cost, for all but special purposes seldom exceeds 20 wt%. Solutions of 0.01 wt% to 1 wt% are demonstrated in Example 2.

In another aspect, the present invention is a composition of matter of the general formula:

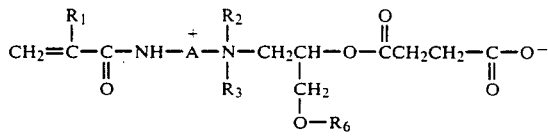

wherein
- $R_1$ is selected from the group consisting of hydrogen and methyl,
- $R_2$ is an alkyl of from 1 to 3 carbon atoms,
- $R_3$ is an alkyl of from 1 to 3 carbon atoms,
- $R_6$ is a linear or branched alkyl of from 7 to 20 carbon atoms, and
- A is a linear alkyl of from 2 to 3 carbon atoms.

Amphoteric monomers of this configuration are conveniently synthesized. In Step 1, a tertiary amine substituted acrylamide monomer is reacted with an alkylene oxide, specifically a glycidyl alkyl ether, and succinnic anhydride. The reaction is carried out in aprotic polar solvent such as acetone, ethyl acetate, tetrahydrofuran, dimethyl formamide, acetonitile, dimethyl sulfoxide, etc. at temperatures of 40° C. to 90° C. and pressures sufficient to maintain all constituents in the liquid phase. No catalyst is required in most cases, however a trace of water or other protic solvent such as ethylene glycol, ethanol, methanol, etc. may be used to initiate reaction.

The reaction may be graphically demonstrated:

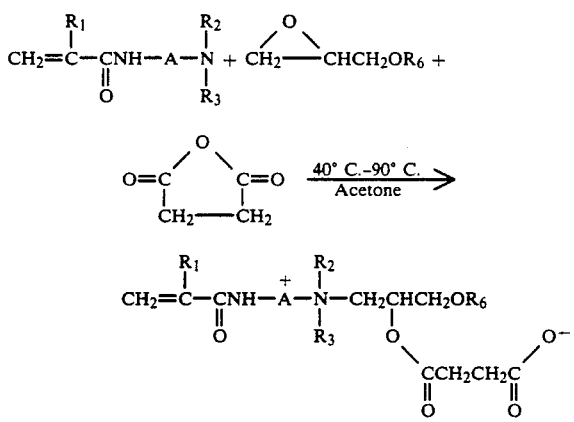

A typical synthesis of these compounds is demonstrated in Example 3.

In another embodiment, this invention relates to solutions. These solutions comprise water and from about 0.01 wt % to about 20 wt % of a monomer characterized by the general formula:

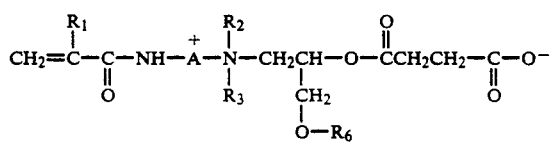

wherein
- $R_1$ is selected from the group consisting of hydrogen and methyl,
- $R_2$ is an alkyl of from 1 to 3 carbon atoms,
- $R_3$ is an alkyl of from 1 to 3 carbon atoms,
- $R_6$ is a linear or branched alkyl of from 7 to 20 carbon atoms, and A is a linear alkyl of from 2 to 3 carbon atoms.

These aqueous solutions display surface and interfacial activity. Example 4 demonstrates solutions in the range of 0.01 wt% to 1 wt% monomer.

These solutions may comprise latex and optionally pigmentation for paint applications. These solutions may alternately comprise brine for applications such as secondary oil recovery and/or detergent adjuvants as described below.

Latex is synthesized by emulsion polymerization carried out in aqueous solution. As seen in Example 6, polymerization can be carried out in solutions of the present invention to produce stable latex emulsions in aqueous media. Such pigments as titanium dioxide, iron oxide, chromium oxide, phthalocyanine blue, Hansa yellow, etc. may also be incorporated into the stable latex containing solutions without loss of stability to produce paints.

Latex containing solutions of the present invention contain typically about 0.01 wt% to about 20 wt% monomer and preferably, about 1 wt% to about 15 wt% with the exact amount determined by the desired composition of the latex copolymer of typically acrylate esters, vinyl acetate and styrene monomers. The use of monomers of the present invention to produce latex in aqueous solution produces internally stabilized polymer emulsions which are inherently superior to those established by added surfactant. This inherent superiority in latex paint formulations is evidenced by mechanical stability of latex lattices, and superior particle size control and film properties. Latex containing solutions of the present invention are stable to electrolyte, organic solvent, mechanical effects and temperatures down to about 4° C.

For detergent purposes, usually the range of concentration is between about 1 wt% to 15 wt% with the residuum being detergent adjuvants described below. In all instances the lower or minimal concentration (0.01% by weight to 0.1% by weight) is referred to as an "effective amount" of surfactant. When these stabilized products are employed as detergents they ordinarily are present in at least the minimal concentrations disclosed accompanied by one or more of the following classes of materials which are generically referred to as detergent adjuvants.

1. Inorganic salts, acids and bases. These are usually referred to as "builders." These salts usually comprise alkalies, phosphates and silicates of the alkali metals as well as their neutral soluble salts. These materials constitute from about 40 to 80 weight percent of the composition in which they are employed.

2. Organic builders or additives—These are substances which contribute to characteristics such as detergency, foaming power, emulsifying power or soil suspending effect. Typical organic builders include sodium carboxymethyl cellulose, sequestering agents such as ethylenediaminetetraacetic acid and the fatty monoethanolamides, etc.

3. Special purpose additives—These include solubilizing additives such as lower alcohols, glycols and glycol ethers, bleaches or brighteners of various structures which share in common that they are dyestuffs and they do not absorb or reflect light in the visible range of the spectrum.

Typical formulations are herein described.

| DETERGENT FORMULATIONS | |
|---|---|
| Parts by wt. | Components |
| A. Dry cleaning composition | |
| 10 | Potassium Oleate |
| 13 | Product Example 1 or 3 |
| 50 | 1,1,2-Trichloroethane |
| 24 | Water |
| 3 | n-Butanol |
| B. Washing Machine Composition | |
| 13 | Product Example 1 or 3 |
| 35 | Sodium Tripolyphosphate |
| 30 | Sodium Silicate |
| 20 | Sodium Carbonate |
| 2 | Sodium Carboxymethyl Cellulose |
| C. Automatic Dishwasher Composition | |
| 5 | Product Example 1 or 3 |
| 34 | Sodium Silicate |
| 61 | Sodium Tripolyphosphate |
| D. Disinfectant and Detergent Composition | |
| 6.3 | Product Example 1 or 3 |
| 45 | Sodium Tripolyphosphate |
| 45 | Sodium Carbonate |
| 3.7 | Oleyl dimethyl ethyl ammonium bromide |

The present invention includes a class of monomers with surface active properties over a range of pH values.

The products of the present invention are useful in household detergent products as well as in an enhanced oil recovery process surfactant formulation. The present invention is most useful as a chemical intermediate that is copolymerized with water soluble monomers such as acrylamide. Monomers of the present invention impart surface active properties to the copolymer product.

The following examples illustrate preparation of typical compounds falling within the scope of the invention. It is understood that these examples are merely illustrative and that the scope of the invention is described in the claims.

EXAMPLE 1

In a 500 ml four neck round bottom flask equipped with mechanical stirrer, dry ice condenser, thermometer and addition funnel, a mixture of dimethylaminopropyl methacrylamide (34 g), 2-dodecen-1-ylsuccinic anhydride (53.3 g) and acetone (150 g) was heated to 50° C. A solution of propylene oxide (14.6 g) in acetone (50 g) was added through the addition funnel over a period of one hour. The reaction mixture was digested at 50° C. over a period of five hours. The completion of the reaction was indicated by a clear solution obtained instantaneously when one drop of reaction mixture was admixed with three milliliters of water. The excess propylene oxide and a small portion of acetone solvent were removed by distillation. The desired product in the form of a solution in acetone was obtained as a bottoms product by a non aqueous titration method (toluene sulfonic acid in acetic acid solvent) found 0.69 meq/g of titratable base (theory 0.70 meq/g). Infra red spectra of the product after stripped off acetone solvent showed carbonyl bands at 5.8 micron typical of ester function and 6–6.6 micron typical of a methacrylamide. These results strongly supported that the expected product was obtained:

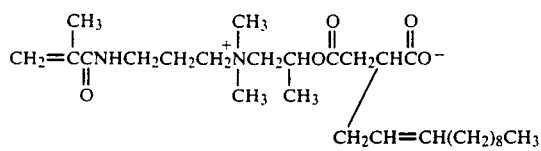

EXAMPLE 2

The surface tension and interfacial tension (water/light mineral oil) of aqueous solution prepared from a sample of solvent free monomer made in Example 1 were measured and results are summarized below.

| Amphoteric Monomer | Surface tension dyne/cm | Interfacial tension dyne/cm |
| --- | --- | --- |
| 1 wt % | 28.4 | 0.9 |
| 0.1 wt % | 28.3 | 0.6 |
| 0.01 wt % | 29.8 | 1.5 |

EXAMPLE 3

In a 500 ml 3-neck round bottom flask equipped with mechanical stirrer, thermometer and addition funnel a mixture of dimethylaminopropyl methacrylamide (34 grams), succinic anhydride (20 grams) and acetone (150 grams) was brought to 50° C. A solution of linear alkyl glycidyl ether (57 grams, equivalent weight 286, Procter and Gamble, Epoxide 8) in acetone (50 grams) was added through the addition funnel over a period of one hour. The reaction mixture was digested at 50° C. for one hour. Analysis of the resulting solution by a non aqueous titration method (toluene sulfonic acid in acetic acid solvent) formed 0.65 meq/g titratable base (theory 0.66 meq/g). Infra red spectra of the product after stripped off acetone solvent showed three types of carbonyl band; ester 5.75 micron, secondary amide 6.0 and 6.5 micron and carboxylate 6.3 micron. These and the remaining bands are consistent with that of the expected product:

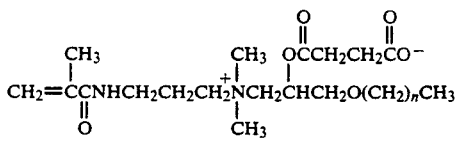

n = 7 to 13

EXAMPLE 4

The surface tension and interfacial tension (water/light mineral oil) of aqueous solution prepared from a sample of solvent free surface active amphoteric monomer made in Example 3 were measured and results are summarized below.

| Amphoteric Monomer | Surface tension dyne/cm | Interfacial tension dyne/cm |
| --- | --- | --- |
| 1.0 wt % | 29.4 | 3.6 |
| 0.1 wt % | 29.0 | 3.9 |
| 0.01 wt % | 32.1 | 5.5 |

EXAMPLE 5

In a field in which the primary production has already been exhausted, an injection well is completed in the hydrocarbon-bearing formation and perforations are formed between the interval of 6890–6910 feet. A production well is drilled approximately 415 feet distance from the injection well, and perforations are similarly made in the same hydrocarbon-bearing formation at 6895–6915 feet.

The hydrocarbon-bearing formation in both the injection well and the production well is hydraulically fractured using conventional techniques, and a gravel-sand mixture is injected into the fracture to hold it open and prevent healing of the fracture.

In the next step oil field brine of 1000 ppm hardness at a temperature of 75° F. containing dissolved therein 1% by weight of the product of Example 1 is injected via the injection well into the formation at a pressure of about 1300 psig and at the rate of 1.05 barrels per minute. Injection of the drive fluid continues at the rate of 1.05 barrels per minute and at the end of 87 days a substantial production of petroleum is achieved.

EXAMPLE 6

A commercially available latex base paint is to be reformulated using monomer of Example 3 to stabilize the latex emulsion. The new paint formulation is as follows:

| | |
| --- | --- |
| Product of Example 3 | 1.9 wt % |
| Ethyl Acrylate | 32.5 wt % |
| Methyl Methacrylate | 16.2 wt % |
| Methacrylic Acid | 0.6 wt % |
| Sodium Persulfate | 1.9 wt % |
| Water | 46.9 wt % |
| | 100.0 wt % |

Water and monomer of Example 3 are charged to a nitrogen blanketed, steam jacketed reaction vessel #1 and heated to 80° C. Ethyl acrylate, methyl methacrylate and methacrylic acid are charged to vessel #2 and thoroughly mixed. Sodium persulfate catalyst is added to vessel #1 along with 3 to 4% of the contents of vessel #2. Vessel #1 is maintained at 80° C. for 10 to 15 minutes with stirring as latex polymerization is initiated. Contents of vessel #2 are pumped into vessel #1 with a metering pump at such a rate that entire addition is completed in 2 to 2½ hours. Temperature is maintained at about 80° C. to 83° C. Once addition is complete, vessel #1 is maintained at 80° C. to 85° C. for an additional ½ hour with stirring. Vessel #1 contents are cooled, pH is corrected with ammonia and pigment is added.

A stable latex emulsion is thereby produced.

EXAMPLE 7

It is desired to treat clay containing bayou water for use in the industrial water system of a petrochemical plant. One thousand gallons per minute of water is introduced into a mixer-settler along with the product of Example 3 monomer in a concentration of 0.01 wt% to 0.1 wt%. The monomer flocculates the clay and thereby causes it to settle. Resulting water is then passed to a clarifier where more flocculated clay settles. A clear, industrial grade water is thereby produced.

The principle of the invention and the best mode contemplated for applying that principle have been described. It is to be understood that the foregoing is illustrative only and that other means and techniques can be employed without departing from the true scope of the invention defined in the following claims.

What is claimed is:

1. A composition of matter characterized by the formula:

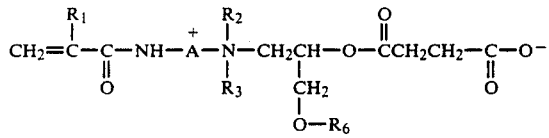

wherein
- $R_1$ is selected from the group consisting of hydrogen and methyl,
- $R_2$ is an alkyl of from 1 to 3 carbon atoms,
- $R_3$ is an alkyl of from 1 to 3 carbon atoms,
- $R_6$ is a linear or branched alkyl of from 7 to 20 carbon atoms, and
- A is a linear alkyl of from 2 to 3 carbon atoms.

2. The composition of matter of claim 1 wherein $R_1$, $R_2$ and $R_3$ are each methyl.

3. The composition of matter of claim 1 wherein $R_6$ is an alkyl of from 8 to 14 carbon atoms.

4. The composition of matter of claim 1 wherein $R_1$, $R_2$ and $R_3$ are each methyl, $R_6$ is an alkyl of from 8 to 14 carbon atoms and A is a linear alkyl of 3 carbon atoms.

5. An aqueous solution comprising water and from 0.01 wt % to 20 wt % of a monomer characterized by the general formula:

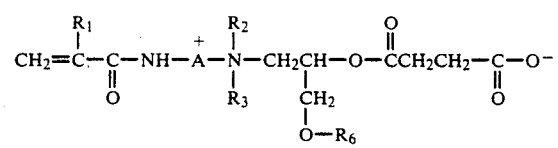

wherein
- $R_1$ is selected from the group consisting of hydrogen and methyl,
- $R_2$ is an alkyl of from 1 to 3 carbon atoms,
- $R_3$ is an alkyl of from 1 to 3 carbon atoms,
- $R_6$ is a linear or branched alkyl of from 7 to 20 carbon atoms, and
- A is a linear alkyl of from 2 to 3 carbon atoms.

6. The solution of claim 5 which additionally comprises latex.

7. The solution of claim 5 which additionally comprises brine.

8. The solution of claim 5 which additionally comprises detergent adjuvants.

9. The solution of claim 5 which comprises from 1 wt % to 15 wt % of monomer.

10. The solution of claim 5 which comprises from 0.01 wt % to 1 wt % of monomer.

* * * * *